US006001353A

United States Patent [19]

Gibori

[11] Patent Number: 6,001,353
[45] Date of Patent: Dec. 14, 1999

[54] 20α-ALPHA-HYDROXY STEROID DEHYDROGENASE RELATED MATERIAL AND METHODS

[75] Inventor: Geula Gibori, Northbrook, Ill.

[73] Assignee: The Board of Trustees of The Univeristy of Illinois, Urbana, Ill.

[21] Appl. No.: 08/853,839

[22] Filed: May 9, 1997

[51] Int. Cl.[6] .................................................. A61K 38/44
[52] U.S. Cl. ....................... 424/94.4; 424/94.1; 435/183; 435/189
[58] Field of Search .............................. 424/184.1, 185.1, 424/94.1, 94.6, 94.4; 435/183, 195, 189

[56] References Cited

U.S. PATENT DOCUMENTS

| 4,006,227 | 2/1977 | Gallegos et al. | 424/195 |
| 4,196,265 | 4/1980 | Koprowski et al. | 435/2 |
| 5,594,104 | 1/1997 | Basinski et al. | 530/324 |

OTHER PUBLICATIONS

Albarracin et al., "Prolactin Action on Leuteal Protein Expression in the Corpus Luteum," *Endocrinology*, 129(4): 1821–1830 (1991).
Albarracin et al., "Identification of a Major Prolactin–Regulated Protein as 20α–Hydroxysteroid Dehydrogenase: Coordinate Regulation of Its Activity, Protein Content, and Messenger Ribonucleic Acid Expression," *Endocrinology*, 134(6):2453–2460 (1994).
Azhar et al., "Characterization of insulin receptor kinase activity and autophosphorylation in different skeletal muscle types," *Am. J. Physiol.*, 260:E1–E7 (1991).
Azhar et al., "Calcium–Activated, Phospholipid–Dependent Protein Kinases from Rat Liver: Subcellular Distribution, Purification, and Characterization of Multiple Forms," *Biochemistry*, 26:7047–7057 (1987).
Bairoch, A., "PROSITE: a dictionary of sites and patterns in proteins," *Nucleic Acids Res.*, 20(Supplement):2013–2018 (1992).
Chomzynski and Sacchi, "Single–Step Method of RNA Isolation by Acid Guanidinium Thiocyanate–Phenol–Chloroform Extraction," *Anal. Biochem.*, 162:156–159 (1987).
Current Protocols in Molecular Biology, Eds., Ausubel et al., Wiley and Sons, New York, pp. 16.12.1–16.14.13 (1996).
De La Llosa–Hermier et al., "20–α–Hydroxysteroid dehydrogenase from pseudopregnant rat ovary: Obtention and characterization of a monoclonal antibody against the enzyme activity," *Biochimie*, 74:1117–1120 (1992).
Duan et al., "Characterization of 20α–Hydroxysteroid Dehydrogenase Expressed in Bacterial and Insect Cell Systems," The Endocrine Society, 77th Annual Meeting, p. 143 (1995) (Abstract P1–124).
Gibori et al., "The Role of Estrogen in the Regulation of Luteal Progesterone Secretion in the Rat After Day 12 of Pregnancy," *Endocrinology*, 100:1483–1495 (1977).
Hakes and Dixon, "New Vectors for High Level Expression of Recombinant Proteins in Bacteria," *Anal. Biochem.*, 202:293–298 (1992).
Hashimoto and Wiest, "Correlation of the Secretion of Ovarian Steroids with Function of a Single Generation of Corpora Lutea in the Immature Rat," *Endocrinology*, 84:873–885 (Apr., 1969).
Iwata et al., "The Purification and Properties of Aldose Reductase from Rat Ovary," *Arch. Biochem. Biophys.*, 282(1):70–77 (Oct., 1990).
Jones and Hsueh, "Direct Stimulation of Ovarian Progesterone–metabolizing Enzyme by Gonadotropin–releasing Hormone in Cultured Granulosa Cells," *J. Biol. Chem.*, 256(3):1248–1254 (Feb., 1981).
Kuhn and Briley, "The Roles of Pregn–5–ene–3β,20α–diol and 20α–Hydroxy Steroid Dehydrogenase in the Control of Progesterone Synthesis preceding Parturition and Lactogenesis in the Rat," *Biochem. J.*, 117:193–201 (1970).
Lacy et al., "Molecular Cloning and Expression of an Abundant Rabbit Ovarian Protein with 20α–Hydroxysteroid Dehydrogenase Activity," *Molecular Endocrinology*, 7(1):58–66 (1933).
Mao et al., "Isolation and Characterization of a Rat Luteal cDNA Encoding 20α–Hydroxysteroid Dehydrogenase," *Biochem. Biophys. Res. Comm.*, 201(3):1289–1295 (Jun. 30, 1994).
Mao et al., "Expression, Purification and Characterization of the Rat Luteal 20α–Hydroxysteroid Dehydrogenase," *Endocrinology*, 138(1):182–190 (1997).
Mitchell et al., "Selectivity of nonsteroid antiinflammatory drugs as inhibitors of constitutive and inducible cyclooxygenase," *Proc. Nat'l Acad. Sci.*, USA, 90:11693–11697 (Dec., 1994).
Miura et al., "Molecular Cloning of cDNA for Rat Ovarian 20α–Hydroxysteroid Dehydrogenase (HSD1)," *Biochem. J.*, 299:561–567 (1994).
Mori and Wiest, "Purification of Rat Ovary 20α–Hyroxysteroid Dehydrogenase by Affinity Chromatography," *J. Steroid Biochem.*, 11:1443–1449 (1979).
Naito et al., "In vitro Secretion of Progestins by Rat Luteal Cells and their 20α–Hydroxysteroid Dehydrogenase Activity," *Endocrinology Jpn.*, 33(1):43–50 (Feb., 1986).
Noda et al., "Purification and characterization of rat ovarian 20α–hydroxysteroid dehydrogenase," *Biochim. et Biophys. Acta*, 1079:112–118 (1991).
Pearson and Lipman, "Improved tools for biological sequence comparison," *Proc. Nat'l Acad. Sci.*, USA, 85:2444–2448 (Apr., 1988).

(List continued on next page.)

*Primary Examiner*—Christina Y. Chan
*Assistant Examiner*—Patrick J. Nolan
*Attorney, Agent, or Firm*—Marshall, O'Toole, Gerstein, Murray & Borun

[57] ABSTRACT

The present invention relates generally to methods of inducing contraceptive or abortive effects via modulation of levels of circulating hormones via administration of an enzyme, pharmaceutical compositions achieving such effects, antibody substances immunoreactive to said enzyme and related substances, and methods for screening for the predisposition of spontaneous abortions

4 Claims, No Drawings

OTHER PUBLICATIONS

Pongsawasdi and Anderson, "Kinetic Studies of Rat Ovarian 20α–Hydroxysteroid Dehydrogenase," *Biochim. et Biophys. Acta.*, 799:51–58 (1984).

Raz and Needleman, "Differential modification of cyclo–oxygenase and peroxidase activities of prostaglandin endoperoxidase synthase by proteolytic digestion and hydroperoxides," *Biochem. J.*, 269:603–607 (1990).

Rodway and Kuhn, "Hormonal Control of Luteal 20α–Hydroxy Steroid Dehydrogenase and $\Delta^5$–3β–Hydroxy Steroid Dehydrogenase during Luteolysis in the Pregnant Rat," *Biochem. J.*, 152:433–443 (1975).

Simonson and Herman, "Protein Kinase C and Protein Tyrosine Kinase Activity Contribute to Mitogenic Signaling by Endothelin–1," *J. Biol. Chem.*, 268(13):9347–9357 (May, 1993).

Srivastava et al., "Antireproductive Effect of Recombinant 20α Hydroxysteroid Dehydrogenase During Pregnancy," *10th International Congress of Endocrinology* (Abstract) (1996).

Talwalker et al., "Maintenance of pregnancy in spayed rats with 20α–hydroxypregn–4–ene–3–one and 20–beta–hydroxypregn–4–ene–3–one," *Nature*, 209(18):86–87 (Jan. 1, 1966).

Webb and Summer, "Expression of Proteins Using Recombinant Baculoviruses," *Technique–A Journal of Methods in Cell and Molecular Biology*, 2(4):173–188 (Aug., 1990).

Weist, W.G., "On the Function of 20α–Hydroxypregn–4–en–3–one During Parturition in the Rat," *Endocrinology*, 83:1181–1184 (1968).

Wiest et al., "Progesterone Catabolism in the Rat Ovary: A Regulatory Mechanism for Progestational Potency During Pregnancy," *Endocrinology*, 82:844–859 (Apr., 1968).

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 1233 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 46..1014

(xi) SEQUENCE DESCRIPTION: SEQ ID NO:1:

```
GGCACGAGAG AAAGCGACTC TTCTAGGGAA GAGCAGCATC TGAGA ATG AAT TCC              54
                                                  Met Asn Ser
                                                   1

AAA ATT CAG AAG ATG GAG TTA AAC GAT GGT CAC TCC ATC CCT GTA CTG           102
Lys Ile Gln Lys Met Glu Leu Asn Asp Gly His Ser Ile Pro Val Leu
        5                  10                  15

GGC TTT GGC ACC TAT GCA ACC GAA GAG AAT CTC AGA AAA AAG TCT ATG           150
Gly Phe Gly Thr Tyr Ala Thr Glu Glu Asn Leu Arg Lys Lys Ser Met
 20              25                  30                  35

GAG TCC ACG AAA ATA GCT ATA GAT GTT GGG TTC CGC CAT ATT GAT TGT           198
Glu Ser Thr Lys Ile Ala Ile Asp Val Gly Phe Arg His Ile Asp Cys
                 40                  45                  50

TCT CAC TTG TAC CAG AAT GAA GAA GAG ATA GGT CAG GCC ATT GTA AGC           246
Ser His Leu Tyr Gln Asn Glu Glu Glu Ile Gly Gln Ala Ile Val Ser
             55                  60                  65

AAG ATT GAA GAT GGC ACT GTG AAA AGG GAA GAT ATA TTC TAT ACT TCA           294
Lys Ile Glu Asp Gly Thr Val Lys Arg Glu Asp Ile Phe Tyr Thr Ser
         70                  75                  80

AAG CTT TGG TCA ACT TCC CAT CGT CCA GAG TTG GTC AGA CCC AGC TTG           342
Lys Leu Trp Ser Thr Ser His Arg Pro Glu Leu Val Arg Pro Ser Leu
 85                  90                  95

GAA AAT TCA CTG AGG AAA CTT AAT TTG GAC TAT GTA GAC CTC TAT CTC           390
Glu Asn Ser Leu Arg Lys Leu Asn Leu Asp Tyr Val Asp Leu Tyr Leu
100                 105                 110                 115

ATT CAT TTC CCG GTA TCT CTG AAG CCA GGG GAT GAG CTT TTA CCT CAA           438
Ile His Phe Pro Val Ser Leu Lys Pro Gly Asp Glu Leu Leu Pro Gln
                120                 125                 130

GAT GAG CAT GGA AAC TTA ATA CTT GAC ACA GTG GAT CTC TGC GAC ACC           486
Asp Glu His Gly Asn Leu Ile Leu Asp Thr Val Asp Leu Cys Asp Thr
            135                 140                 145

TGG GAG GCC ATG GAG AAG TGT AAG GAT GCA GGA TTG GCC AAG TCC ATC           534
Trp Glu Ala Met Glu Lys Cys Lys Asp Ala Gly Leu Ala Lys Ser Ile
        150                 155                 160

GGG GTG TCC AAC TTT AAC CGC AGG CAG CTG GAG AAG ATC CTG AAT AAG           582
Gly Val Ser Asn Phe Asn Arg Arg Gln Leu Glu Lys Ile Leu Asn Lys
165                 170                 175

CCG GGG CTC AAG CAC AGG CCT GTG TGC AAC CAG GTA GAA TGC CAT CTT           630
Pro Gly Leu Lys His Arg Pro Val Cys Asn Gln Val Glu Cys His Leu
180                 185                 190                 195

TAT CTC AAC CAG AGC AAG CTG CTC GCT TAC TGC AAG ATG AAT GAC ATC           678
Tyr Leu Asn Gln Ser Lys Leu Leu Ala Tyr Cys Lys Met Asn Asp Ile
                200                 205                 210

GTT CTG GTT GCC TAT GGT GCC CTG GGA ACT CAG AGA TAC AAA TAC TGT           726
Val Leu Val Ala Tyr Gly Ala Leu Gly Thr Gln Arg Tyr Lys Tyr Cys
            215                 220                 225

ATT AAT GAA GAT ACC CCA GTT CTC TTG GAT GAT CCC ATT CTT TGT ACC           774
Ile Asn Glu Asp Thr Pro Val Leu Leu Asp Asp Pro Ile Leu Cys Thr
        230                 235                 240
```

-continued

```
ATG GCA AAG AAG TAC AAG CGG ACT CCA GCC CTG ATT GCC CTT CGC TAC      822
Met Ala Lys Lys Tyr Lys Arg Thr Pro Ala Leu Ile Ala Leu Arg Tyr
    245                 250                 255

CAG CTG GAG CGT GGG ATT GTG ACC CTA GTC AAG AGT TTC AAT GAG GAG      870
Gln Leu Glu Arg Gly Ile Val Thr Leu Val Lys Ser Phe Asn Glu Glu
260                 265                 270                 275

AGA ATC AGA GAG AAC CTG CAG GTC TTT GAT TTC CAG TTG GCT TCA GAT      918
Arg Ile Arg Glu Asn Leu Gln Val Phe Asp Phe Gln Leu Ala Ser Asp
                280                 285                 290

GAC ATG GAA ATT TTA GAT AAC CTG GAC AGA AAT CTT CGG TAC TTT CCT      966
Asp Met Glu Ile Leu Asp Asn Leu Asp Arg Asn Leu Arg Tyr Phe Pro
                    295                 300                 305

GCT AAT ATG TTT AAG GCT CAC CCT AAC TTT CCA TTC TCT GAT GAA TAC     1014
Ala Asn Met Phe Lys Ala His Pro Asn Phe Pro Phe Ser Asp Glu Tyr
                310                 315                 320

TAAGATGGCA GCCCTAGCCA TGAGTTCTGC TCGAAGCTCC TTTGTGTGAT GCTCGACTCT   1074

CAGAGGCCAA TAATACAACA CACTGACTCC AATCCATACT GCTTAGCAAC TCACCCCCAG   1134

TTTGAGCTGT GTCTGTACAT CGGGGAGCAA ATTCACTAAA TTTTCCTGCT TTTCTGTAAA   1194

TAAATAAAAA TATTTTGCTT CAAAAAAAAA AAAAAAAA                           1233
```

(2) INFORMATION FOR SEQ ID NO:2:

(i) SEQUENCE CHARACTERISTICS:
        (A) LENGTH: 323 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asn Ser Lys Ile Gln Lys Met Glu Leu Asn Asp Gly His Ser Ile
  1               5                  10                  15

Pro Val Leu Gly Phe Gly Thr Tyr Ala Thr Glu Glu Asn Leu Arg Lys
                 20                  25                  30

Lys Ser Met Glu Ser Thr Lys Ile Ala Ile Asp Val Gly Phe Arg His
             35                  40                  45

Ile Asp Cys Ser His Leu Tyr Gln Asn Glu Glu Glu Ile Gly Gln Ala
         50                  55                  60

Ile Val Ser Lys Ile Glu Asp Gly Thr Val Lys Arg Glu Asp Ile Phe
 65                  70                  75                  80

Tyr Thr Ser Lys Leu Trp Ser Thr Ser His Arg Pro Glu Leu Val Arg
                 85                  90                  95

Pro Ser Leu Glu Asn Ser Leu Arg Lys Leu Asn Leu Asp Tyr Val Asp
                100                 105                 110

Leu Tyr Leu Ile His Phe Pro Val Ser Leu Lys Pro Gly Asp Glu Leu
            115                 120                 125

Leu Pro Gln Asp Glu His Gly Asn Leu Ile Leu Asp Thr Val Asp Leu
        130                 135                 140

Cys Asp Thr Trp Glu Ala Met Glu Lys Cys Lys Asp Ala Gly Leu Ala
145                 150                 155                 160

Lys Ser Ile Gly Val Ser Asn Phe Asn Arg Arg Gln Leu Glu Lys Ile
                165                 170                 175

Leu Asn Lys Pro Gly Leu Lys His Arg Pro Val Cys Asn Gln Val Glu
            180                 185                 190

Cys His Leu Tyr Leu Asn Gln Ser Lys Leu Leu Ala Tyr Cys Lys Met
        195                 200                 205
```

```
Asn Asp Ile Val Leu Val Ala Tyr Gly Ala Leu Gly Thr Gln Arg Tyr
    210             215                 220

Lys Tyr Cys Ile Asn Glu Asp Thr Pro Val Leu Leu Asp Asp Pro Ile
225             230                 235             240

Leu Cys Thr Met Ala Lys Lys Tyr Lys Arg Thr Pro Ala Leu Ile Ala
            245             250                 255

Leu Arg Tyr Gln Leu Glu Arg Gly Ile Val Thr Leu Val Lys Ser Phe
        260             265             270

Asn Glu Glu Arg Ile Arg Glu Asn Leu Gln Val Phe Asp Phe Gln Leu
        275             280             285

Ala Ser Asp Asp Met Glu Ile Leu Asp Asn Leu Asp Arg Asn Leu Arg
    290             295             300

Tyr Phe Pro Ala Asn Met Phe Lys Ala His Pro Asn Phe Pro Phe Ser
305             310             315             320

Asp Glu Tyr
```

20α-ALPHA-HYDROXY STEROID DEHYDROGENASE RELATED MATERIAL AND METHODS

U.S. GOVERNMENT RIGHTS

Work described herein was supported by a National Institutes of Health research grant, HD11119.

FIELD OF THE INVENTION

The present invention relates generally to methods of inducing contraceptive or abortive effects by modulating levels of circulating hormones via administration of an enzyme, pharmaceutical compositions achieving such effects, antibody substances immunoreactive with said enzyme, and methods for screening for individuals predisposed to spontaneous abortions.

BACKGROUND OF THE INVENTION

Progesterone is a steroid essential for the maintenance of normal pregnancy in mammals, including primates. Among other things, progesterone: (a) causes development of decidual cells in the uterine endometrium which are important in nutrition of the early embryo; (b) increases secretion of nutritive substances in the uterus and fallopian tubes to aid in the development of the zygote prior to implantation; and (c) reduces the risk of spontaneous abortions via a decrease in contractility of the uterus. Thus, removal of progesterone from circulation before implantation or nidation (embedding of the early embryo into the uterine mucosa) can prevent implantation whereas removal after nidation can prevent normal maintenance of pregnancy.

Progesterone is mainly, although not exclusively, metabolized in the liver to the principal metabolite, 5β-pregnane-3α,20α-diol. While 5β-pregnane-3α,20α-diol is the principle metabolite, progesterone is also metabolized by the ovaries. Specifically, the 20-oxo group is reduced to, among other substances, 20β-hydroxypregn-4-ene-3-one (i.e., 20α-hydroxyprogesterone). 20α-hydroxyprogesterone, unlike progesterone, is biologically inactive and cannot maintain pregnancy or even allow implantation to occur [Talwalker et al., *Endocrinology* 74:86–87 (1966); Wiest et al., *Endocrinology* 82:844–859 (1968)].

Presently, the only safe abortifacient available is the progesterone antagonist, mifepristone (RU 486). When administered early in pregnancy, mifepristone's main mechanism of action is to cause decidual breakdown by blockade of uterine progesterone receptors. However, for mifepristone to cause a complete abortion, a prostaglandin must be administered approximately 48 hours after mifepristone administration to further increase uterine contractions and ensure expulsion of the detached blastocyst. Therefore, there remains an interest for a novel substance that can not only induce abortion but also prevent implantation and pregnancy without the side effects or drawbacks of the currently available agent.

The enzyme responsible for the ovarian metabolism of progesterone to 20α-hydroxyprogesterone is 20α-hydroxysteroid dehydrogenase (20α-HSD). Specifically, 20α-HSD is nicotinamide adenine dinucleotide phosphate (NADPH)-dependent and catalyzes the transfer of hydrogen from NADPH to progesterone.

By metabolizing progesterone to an inactive form, 20α-HSD plays a central role in inhibiting the maintenance of pregnancy and prevention of implantation [Wiest, *Endocrinology* 83:1181–184 (1968); Wiest et al., *Endocrinology* 82:844–859 (1968); Kuhn and Briley, i *Biochem. J.* 0117:193–200 (1970); Rodway and Kuhn, *Biochem. J.* 152:433–443 (1975)]. Further supporting this role is the fact that it is the increase in ovarian 20α-HSD activity rather than a decrease in the synthesis of progesterone that contributes to the lower circulating progesterone levels associated with the termination of pregnancy [Kuhn and Briley, *Biochem. J.* 117:193–201 (1970)]. Indeed, 20α-HSD gene expression [Albarracin et al. *Endocrinology* 134:2453–2460 (1994)] and activity remains repressed throughout pregnancy but are induced before parturition [Wiest et al., *Endocrinology* 82:844–859 (1968); Kuhn and Briley, *Biochem. J.* 117:193–200 (1970]. Also, ovarian 20α-HSD catalyzes the decline in progesterone levels which occur during normal and induced termination of pregnancy and pseudopregnancy [Hashimoto and Wiest, *Endocrinology* 84:873–885 (1969); Naito et al., *Endocrinology Jpn* 33(1):43–50 (February 1986)].

While 20α-HSD is of much interest as a key enzyme in the termination/prevention of pregnancy, it is possible that the enzyme is also of importance in spontaneous abortions. Specifically, it is possible that a significant number of spontaneous abortions are due to early expression of 20α-HSD. Therefore, detection of early 20α-HSD expression would be of interest in those susceptible to early spontaneous abortions. If detection is made early enough, progesterone replacement therapy could be initiated to help maintain the pregnancy.

Since ovarian 20α-HSD has been identified as a key enzyme in the metabolism of progesterone, efforts have been undertaken to characterize the structural/functional aspects of the enzyme. However, these efforts have been hampered by the limited availability of the purified native form of the enzyme. Further, purified native enzyme is unsuitable for the studies designed to evaluate the role of post-translational events such as glycosylation and phosphorylation in enzyme activity. In order to avoid the limitations of using native 20α-HSD, cloning of the gene encoding the rat corpus luteum 20α-HSD has been undertaken and accomplished [Mao et al. *Biochem. Biophys. Res. Comm.* 201(3):1289–1295 (1994)]. The use of recombinant methods to produce 20α-HSD overcomes the limitations inherent in the use of native enzyme and provides an abundant source of the enzyme for a variety of uses.

These uses include, but are not limited to (1) obtaining a recombinant protein which can be used to inhibit the maintenance of pregnancy and/or prevent implantation leading to pregnancy and (2) obtain antibodies to the protein which can be used as a diagnostic agent to detect circulating levels of the protein in individuals at risk for spontaneous abortions.

SUMMARY OF INVENTION

The present invention is directed to a method of inducing abortion or preventing nidation in mammals by reduction of circulating blood levels of progesterone. Progesterone levels are reduced by administration of 20α-HSD, an enzyme which metabolizes progesterone to an inactive form. NADPH may be co-administered 20α-HSD. Route of administration may be oral, intramuscular, subcutaneous, intraperitoneal, intravenous, or by other well known routes of administration. Osmotic mini-pumps and timed-release pellets or other depot forms may also be used.

In another aspect the present invention is directed to antibody substances that are immunoreactive with 20α-HSD and to the use of the antibodies in a method of detecting levels of 20α-HSD. Such antibodies are useful for screening for individuals predisposed to spontaneous abortions. Also provided by this invention is a diagnostic test kit for ascertaining serum levels of 20α-HSD.

A further aspect of the present invention involves a pharmaceutical composition comprising 20α HSD in a pharmaceutically acceptable carrier, diluent and/or adjuvant. The pharmaceutical composition may be used to produce abortion or to prevent nidation or for other uses.

In another aspect, the invention is directed to antibodies that are immunoreactive with 20α-hydroxyprogesterone (a metabolite of the reduction of progesterone by 20α-HSD) and to the use of the antibodies in a method of detecting levels of 20α-hydroxyprogesterone. Such antibodies are useful for screening for individuals predisposed to spontaneous abortions. Also provided by this invention is a diagnostic test kit for ascertaining serum levels of 20α-hydroxyprogesterone.

In a further aspect, the present invention is directed to methods for ascertaining serum levels progesterone or screening for individuals predisposed to spontaneous abortions. Also provided by this invention is a diagnostic test kit for determining serum levels of progesterone.

Another embodiment of the invention is directed to modulators of 20α-HSD activity. Such modulators may have any of a variety of mechanisms of action. Such modulators may covalently modify the enzyme for example by glycosylation or by other modifications.

Further aspects of the invention and embodiments will be apparent to those skilled in the art. In order that the present invention is fully understood, the following examples are provided by way of exemplification only and not by way of limitation.

DETAILED DESCRIPTION

Among its advantages, the present invention provides (1) a novel method of inducing abortion or preventing nidation by the reduction of progesterone levels via administration of 20α-HSD, (2) novel methods for screening for individuals predisposed to spontaneous abortions, and (3) antibody substances immunoreactive with 20α-HSD and 20α-hydroxyprogesterone.

Example 1 describes the isolation and characterization of rat luteal cDNA encoding 20α HSD. Example 2 is directed to the expression and purification of recombinant or non-naturally occurring 20α-HSD from bacterial and/or insect cell expression systems. Example 3 sets forth the characterization of the recombinant 20α-HSD produce in Example 2. Example 4 relates to antibodies to 20α-HSD and to progesterone metabolites. Example 5 is directed to methods for screening for individuals predisposed to spontaneous abortions. Example 6 is related to the anti-reproductive effect of recombinant 20α-HSD during pregnancy.

The following examples are illustrative of the processes and products of the present invention but are not to be construed as limiting.

EXAMPLE 1

Isolation And Characterization of Rat Luteal cDNA encoding 20α-HSD

The isolation and characterization of cDNA (rat corpus luteum) encoding for 20α-HSD described herein was described by Mao et al. [*Biochem. Biophys. Res. Comm.* 201(3):1289–1295 (1994)]. In sum, a λ Zap II rat cDNA library was screened using both an antibody to rat 20α-HSD and a rabbit 20α-HSD cDNA. Further, a full length cDNA was isolated and sequenced. In addition, the isolated cDNA was used to examine the tissue specific expression of 20α-HSD and the role of prolactin on the abundance of 20α-HSD mRNA.

A. Isolation: Library Construction and Screening

An oligo(dT) primed cDNA expression library made from corpus luteum mRNA of day 7 hypophysectomized pregnant rats was constructed in λ Zap II (Stratagene, La Jolla, Calif.). The library was initially screened with rat 20α-HSD antiserum [Albarracin et al., *Endocrinology*, 129:1821–1830; (1991) and Albarracin et al., *Endocrinology* 134:2453–2460; (1994)] using the pico-Blue Immunoscreening Kit (Stratagene, La Jolla, Calif.). Approximately $5\times10^5$ phages were screened. Positive plaques were isolated and rescreened by standard filter hybridization with rabbit 20α-HSD cDNA [Lacy et al., *Molecular Endocrinology* 7:58–66 (1993)] labeled with $^{32}P$. Filters were prehybridized, hybridized ($10^6$ cpm/ml) in a 2×PIPES buffer containing 50% formamide, 0.5% SDS and 100 µg/ml salmon sperm DNA for 12–16 hours at 42° C., washed twice in 2×SSC and 0.1% SDS at room temperature for 15 minutes, twice in 0.2×SSC and 0.1% SDS at 42° C. for 15 minutes, and finally twice in 0.1×SSC and 0.1% SDS at 42° C. for 15 minutes. Secondary and tertiary screenings were performed until all plaques were positive. Nine of the 33 positive clones were isolated. pBluescript SK(−) containing the insert was excised in vivo by R408 helper phage to produce pBluescript double-stranded phagemids.

B. Isolation: DNA Sequencing and Analysis

20α-HSD cDNA was sequenced using the Sequenase Kit (United States Biochemical, Inc., Cleveland, Ohio). The sequence was extended by a primer-directed dideoxy sequencing approach with sequence specific oligonucleotide primers (National BioScience, Plymouth, Minn.). Two clones were completely sequenced and the cDNA sequence was determined from both strands. DNA and deduced amino acid sequence analysis was performed using the FastA program [Pearson and Lipman, *Proc. Natl. Acad. Sci. USA*, 85:2444–2448 (1988)] with GenBank® and PIR® databases, respectively. The PROSITE [Bairoch, *Nucleic Acids Res.*, 20:2013–2018 (1992)] program was used to identify protein patterns or motifs in the protein sequence.

C. Isolation: Results

A full length 1233 bp 20α-HSD cDNA was isolated and the complete nucleotide sequence is shown as SEQ ID NO. 1 with the deduced amino acid sequence presented as SEQ ID NO. 2.

The 20α-HSD cDNA (SEQ ID NO. 1) contained an open reading frame of 969 nucleotides, a single in-frame ATG initiation codon, a stop codon at nucleotide 1015 and a poly($A^+$) stretch at the 3' end. The deduced amino acid sequence (SEQ ID NO. 2) of the protein was shown to be composed of 323 amino acids, having a molecular weight of 37,268 daltons. Further, the amino acid composition deduced from the cDNA matched that obtained from an amino acid analysis performed on the purified 20α-HSD previously reported by Albarracin et al. [*Endocrinology* 134(6):2453–2460 (1994)].

D. Characterization: Tissue RNA Isolation and Northern Blot Analysis

As it has been previously reported that 20α-HSD is prolactin regulated (id.), the isolated 20α-HSD cDNA was used to examine the tissue specific expression of 20α-HSD and the role of prolactin in the abundance of 20α-HSD mRNA.

For these studies, Holtzman pregnant rats were hypophysectomized on day 3 and treated with either prolactin (NIADDK oPRL-18, 125 µg, twice daily) or with vehicle (control). On day 7, corpus luteum and various other tissues (brain, decidua, ovary, and uterus) were obtained for analysis.

Total RNA from the harvested tissues was isolated by the method of Chomzynski and Sacchi [Anal. Biochem. 162:156–159 (1984)] and equal aliquots (20 µg) were electrophoresized and transferred to nylon membranes, or slot blotted onto Genescreen (DuPont, Wilmington, Del.) membrane. RNA was prehybridized for 16 hours at 42° C. in 40% formamide, 6×SSC, 5×Denhardt's, 20 mM NaH$_2$PO$_4$, 0.2% SDS and 100 µg/ml salmon sperm DNA. Hybridization was completed in the same solution with the addition of $^{32}$P-labeled rat 20α-HSD cDNA (10$^6$ cpm/ml) at 42° C. for 12–16 hours. Blots were washed twice in 05.×SSC and 0.1% SDS (15 minutes, room temperature), twice in 0.2×SSC and 0.1% SDS (15 minutes, 42° C.), twice in 0.2×SSC and 0.1% SDS (15 minutes, 56° C.) and twice in 01.×SSC and 0.1% SDS (15 minutes, 56° C.).

E. Characterization: Results

Northern analysis revealed that the rat 20α-HSD cDNA specifically hybridized to a single 1.2 Kb 20α-HSD mRNA transcript in corpora lutea and that prolactin pretreatment markedly reduced expression of 20α-HSD mRNA correlating perfectly with earlier results seen with the enzyme [Albarracin et al., *Endocrinology*, 129:1821–1830 (1991) and Albarracin et al., *Endocrinology* 134:2453–2460 (1994)].

Although 20α-HSD was detected in both the corpus luteum and whole ovaries of hypophysectomized pregnant rats, levels in the ovary were lower than in the isolated corpus luteum due to the fact that non-luteal tissues of the pregnant rat do not express 20α-HSD [id.]. Hybridization analysis performed on the corpus luteum of intact rats clearly indicated that the 20α-HSD gene is not expressed in corpus lutea that are actively secreting progesterone, but increases markedly after the corpus luteum undergoes luteolysis.

EXAMPLE 2

Expression and Purification of Recombinant 20α-HSD From Bacterial and Insect Cells In addition to the specific examples demonstrated below, other prokaryotic and eukaryotic expression systems may be used to express a non-naturally occurring 20α-HSD protein. [see *Current Protocols in Molecular Biology*, Eds. Ausubel et al., Wiley and Sons, New York, 16.12.1–16.14.13 (1996) and U.S. Pat. No. 5,594,104, incorporated herein by reference].

A. Bacterial Cells: Plasmid Construction

Standard procedures of DNA manipulation and transfection were used to construct plasmids and expression vectors [Sambrook et al., *Molecular Cloning: A laboratory manual*, Cold Spring Harbor Laboratory Press, Cold Spring Harbor, N.Y. (1989)]. More particularly, a DNA fragment of 1.2 Kb containing the entire coding region of 20α-HSD was removed from pBluescript vector by EcoRI and XhoI digestion. The purified EcoRI-XhoI fragment was then ligated into the EcoRI and XhoI cloning sites of the pGEX-4T-2 vector (Pharmacia, Piscataway, N.J.), which is a glutathione-s-transferase (GST) fusion protein expression vector. The construct was then transfected into a bacterial host, *E. coli* DH5α. Although other bacterial hosts may be used. The correct orientation of the translational reading frame for GST-20α-HSD fusion protein was confirmed by DNA sequencing.

B. Bacterial Cells: Expression and Purification of Expressed 20α-HSD

200 µl of overnight culture containing the expression vector described above (*E. coli* DH5α transfected with GST-20-HSD cDNA) was inoculated into 200 ml fresh, prewarmed 2×YTG medium (16 g/L tryptone, 10 g/L yeast extract and 5 g/l NaCl) containing 100 mg/ml of ampicillin. The culture was incubated at 37° C. with shaking until an absorption reading between 1.2 and 2.0 at 600 nm was achieved. Subsequently, isopropyl-β-D-thiogalactopyranoside (IPTG) was added to a final concentration of 01 nM. The incubation was continued for an additional 4 hours. The culture was centrifuged and the pelleted bacteria were resuspended in PBS/Triton X-100, sonicated and mixed gently at room temperature for 30 minutes. The suspension was then centrifuged at 1200×g for 10 minutes. The supernatant containing recombinant 20α-HSD-GST fusion protein was further processed to obtain pure 20α-HSD using standard protocols [Hakes and Dixon, *Anal. Biochem.* 202:293–298 (1992)].

Briefly, a 50% slurry of glutathione Sepharose 4B beads was mixed with supernatant (approximately 2 ml of the 50% slurry of beads to each 100 ml supernatant) and agitated at room temperature. At the end of the incubation, the beads were collected by centrifugation and washed several times with 10 volumes of PBS. After final centrifugation, the glutathione beads (approximately 2 ml) with bound 20α-HSD-GST fusion protein were resuspended in 1 bed volume of PBS and digested with 500 cleavage units of bovine plasma thrombin at room temperature for 16 hours. After thrombin cleavage of the fusion protein, the beads with bound GST were separated from the recombinant 20α-HSD protein by centrifugation at 10,000×g for 10 minutes at 4° C. Typically, 500 µg of recombinant 20α-HSD was obtained from 200 ml of bacterial cell culture.

C. Insect Cells: Construction of a 20α-HSD cDNA-containing Baculovirus Transfer Vector; Transfection and Isolation of Recombinant Baculovirus The expression and purification of recombinant 20α-HSD from insect cells described herein was previously undertaken and demonstrated by Mao et al. [*Endocrinology*, 138(1):182–190 (1997)].

A vector containing rat luteal 20α-HSD cDNA clone was digested with XhoI and blunt ended with Klenow DNA polymerase. Thereafter, a 20α-HSD cDNA fragment was excised using BamH1. The resulting 1.2 Kb fragment was then inserted into the pBlueBacIII vector to create pBlueBacIII-20α-HSD. The cDNA insert of 20α-HSD is located immediately downstream of the polyhedrin promotor. The correct orientation of 20α-HSD cDNA in pBlueBacIII-20α-HSD was analyzed by DNA sequencing and was shown to be correct.

Recombinant baculovirus, AcNPV [*Autographa californica* nuclear polyhidrosis virus; In Vitrogen, Inc., San Diego, Calif.] containing the 20α-HSD sequence under the transcriptional control of the polyhedrin promotor was produced by in vivo homologous recombination via the method of Webb and Summer [*Technique* 2:173–188 (1990)].

In order to express 20α-HSD, 2 µg of the pBlueBacIII-20α-HSD vector described above were mixed with 1 mg of linearized wild type AcNPV viral DNA and co-transfected into *Spodoptera frugiperda* [Sf-9; In Vitrogen, Inc., San Diego, Calif. insect cells by cationic liposome-mediated gene transfer according to the protocol suggested by the manufacturer. After 120 hours post-infection, the medium was collected, centrifuged, diluted 10 to 10,000-fold and then used to infect a fresh monolayer of Sf-9 cells. To facilitate the identification of viral plaques, a layer of 0.625% agarose containing 75 μg/ml X-Gal (5-bromo-4-chloro-3-inolyl-β-D glactopyranoside was applied to the transfected cells. After 6–8 days, recombinant viruses, designated AcNPV-20α-HSD, were detected by the formation of blue plaques. Several blue plaques were picked and subjected to three cycles of plaque purification until cells with inclusion bodies were not detected. After purification, several strains of recombinant AcNPV's were obtained.

D. Insect Cell Culture: Expression and Purification of 20α-HSD

Sf-9 insect cells were maintained in Grace's medium (GIBCO BRL Products, Gaithersburg, Md.) supplemented with 10% fetal bovine serum, supplemented with yeastolate (3.3 g/L), lactalbumin hydrolysate (3.3 g/L; Intermedia), gentamycin (50 μg/ml; Sigma Chemical Co., St. Louis, Mo.) and fungizone (2.5 μg/ml;GIBCO BRL Products, Gaithersburg, Md.) in monolayer or suspension culture.

The Sf-9 cells were seeded at a density of $2-2.5 \times 10^6$ per 60 mm dish or $9 \times 10^6$ cells per 75 $cm^2$ flask in Grace's medium. After the cells were attached, the medium was removed and a volume of virus inoculum sufficient to infect the cells (in log phase of growth) at a multiplicity of 3 or 4 to 1 was added. After incubation at 27° C. for 1.5 hours, the inoculum was replaced with fresh Grace's medium and incubated at 27° C. for up to 5 days; infected insect cells were collected and used for purification of recombinant 20α-HSD.

Recombinant 20α-HSD was purified by the combination of procedures described by Noda et al. [Biochim Biophys. Acta. 1079:112–118 (1986)] and De La Llosa-Hermier et al. [Biochimie 784:1117–1120 (1992)]. In brief, the culture was centrifuged and the resulting pellet was resuspended in 30 ml of homogenization buffer containing 10 mM potassium phosphate buffer (pH 8.0), 1 mM EDTA and 10 mM dithiothreitol (Buffer A), homogenized in a Potter-Elvehjem homogenizer at 4° C. The homogenate was sonicated and centrifuged for 10 minutes at 1,000×g to remove nuclei, unbroken cells and cell debris. The supernatant from the low speed spin was centrifuged for 1 hour at 100,000×g and the resultant supernatant was loaded onto a DEAE-cellulose column (1.6×10 cm) that had been previously equilibrated with buffer A. The columns was eluted with a 120 ml liners gradient of NaCl (0–500 mM) in the equilibration buffer. The fractions containing the enzyme activity (detected by spectrophotometric assay method, described below) were pooled, concentrated and dialyzed against buffer A. After dialysis, the sample was applied to a 1.2×12 cm Matrex Gel Green dye affinity column [GIBCO BRL, Gaithersburg, Md.] pre-equilibrated with buffer A. The active fractions were combined, concentrated by ultrafiltration dialyzed against buffer A and further purified by affinity chromatography on Red-Sepharose (1.2×10 cm). The enzyme was eluted from the column in buffer A containing 1 mM NADPH. Fractions containing the enzyme were combined, concentrated and dialyzed against buffer A containing 20% glycerol before storage at −80° C.

EXAMPLE 3

Characterization/Analysis of Recombinant 20α-HSD

The characterization and analysis of the non-naturally occurring (recombinant) 20α-HSD from a bacterial expression system or an insect expression system described herein was previously reported by Mao et al. [Endocrinology, 138(1):182–190 (1997)].

A. Immunoblot Analysis

Immunoblotting of expressed recombinant 20α-HSD (either from the bacterial or insect expression systems) was performed using the polyclonal 20α-HSD anti-rat antibody [Albarracin et al. Endocrinology, 134(1):2453–2460 (1994)]. The fusion protein expressed in either E. coli or Sf9 cells (see Example 2, above) were subjected to SDS-PAGE under reducing conditions on a gel containing 7.5% polyacrylamide and then transferred to a nitrocellulose membrane. After transfer, the blots were blocked with 3% BSA and then probed with the anti-20α-HSD antibody or preimmune serum. The immunoreactive proteins were visualized using alkaline phosphatase conjugated anti-rabbit IgG as a secondary antibody. Results indicated a protein form of having a molecular mass of approximately 37 kDa. This result agreed with the calculated molecular mass of the encoded protein [Mao et al., Biochem. Biophys. Res. Com. 201:1289–1295 (1994)] and with the native enzyme detected in the corpus luteum [Albarracin et al., Endocrinology 134:2453–2460 (1994)].

B. 20α-HSD Activity

Enzyme activity of the recombinant 20α-HSD was determined by the rate of conversion of $[1-2^3H]$-20α-hydroxy-pregn-4-ene-3-one (20α-hydroxprogesterone) to $[1,2^3H]$ progesterone in the presence of NADPH as described by Jones & Hsueh [J. Biol. Chem. 256:1248–1254 (1981)]. Enzyme activity was measured in this manner due to the fact that in an in vitro setting the reaction may be reversed, i.e. conversion of 20α-hydroxyprogesterone to progesterone. The assay mixtures (0.05 ml) contained 100 μM $[1,2^3H]$ hydroxyprogesterone [Dupont-New England Nuclear Research Products, Boston Mass.] (approximately $1 \times 10^6$ DPM), 0.1 M Tris-HCl, pH 8.0; 0.5 mM dithiothreitol, 1 mM EDTA, 10 mM nicotinamide, 300 μM NADP and from about 0.025 to about 2.5 μg of purified recombinant 20α-HSD, prepared as described above. Following incubation at 37° C. for 30 minutes, the [$^3$H]progesterone content of each sample was determined after isolation by thin layer chromatography isolation. One unit of enzyme activity is defined as that amount of enzyme catalyzing the formation of 1 nmol of [$^3$H]progesterone/minute from $[1,2^3H]$ hydroxyprogesterone. Specific activity is expressed as units/min/mg protein. The protein concentration was determined by the Bradford method using bovine serum albumin [Sigma Chemical Co, St. Louis, Mo.] as the standard [Bradford, Anal. Biochem. 72:248–254 (1976)]. In some cases, enzyme activity was also determined spectrophotometrically either by measuring the reduction of NADP or oxidation of NADPH [Mori et al., J. Steroid Biochem. 11:1443–1449 (1979); Pongsawasdi et al., Biochim Biophys. Acta. 799:51–58 (1984); Noda et al., Biochim Biophys. Acta. 1079:112–118 (1991)].

The purified preparation of non-naturally occurring 20α-HSD from the bacterial expression system showed high levels of enzymatic activity. More particularly, the average specific activity of the purified preparations was 332 ±47 nmol/min/mg protein, and activity was concentration (enzyme protein) and time dependent. Enzyme activity was not detected using the GST-20α-HSD fusion protein alone.

Sf-9 cells infected with the recombinant baculovirus (see Example 1, Parts C-D) containing 20α-HSD cDNA (AcNPV/20α-HSD) were assayed for 20-α-HSD activity as a function of days post-infection. Results indicated enzyme activity in the total cell lysates was maximal (750–893 pmol/min/mg protein) at 2 days post-infection, with a steady and substantive decline in 20α-HSD activity between days 3–6.

C. Aldose/Aldehyde Reductase and Prostaglandin Synthase Activities

Since the cDNA and predicted amino acid sequence of the rat luteal 20α-HSD is related to bovine lung $PGF_{2\alpha}$ synthase and aldose/aldehyde reductase ($PGF_{2\alpha}$ synthase: 75% nucleotide identity and 69% amino acid identity, aldose/aldehyde reductase: less than 50% nucleotide sequence homology, [Mao et al. *Biochem. Biophys. Res. Comm.* 201:1289–1295, 1994; Miura et al. *Biochem. J.* 299:561–567, 1994 and Lacy et al. *Mol. Endocrinol.* 7:58–66, 1993], analysis was conducted to see whether recombinant 20α-HSD was active as a aldose/aldehyde reductase and/or prostaglandin endoperoxide synthase.

To test for prostaglandin endoperoxide synthase type catalytic activity of recombinant 20α-HSD, both cyclooxygenase activity (which converts arachidonic acid into the hydroperoxide, $PGG_2$) and peroxidase activity (which reduces $PGG_2$ and other hydroperoxides to the corresponding alcohol, such as $PGH_2$) were measured. The cyclooxygenase assay was performed by following the conversion of [$^3$H] arachidonic acid [Dupont-New England Nuclear Research Products, Boston, Mass.] to [$^3$H]$PHG_2$ and [$^3$H]PHE2 [Mitchell et al. *Proc. Natl. Acad. Sci. USA* 90:11693–11697, 1994]. Peroxidase activity was measured by monitoring the oxidation of N,N,N',N', tetramethyl-p-phenylenediamine at 611 nm [Iwata et al., *Arch. Biochem. Biophys.* 282:70–77 (1990)]. Neither peroxidase not cyclooxygenase activity was detected in the purified preparations recombinant 20α-HSD from either expression systems.

Aldo-keto reductase activity of the recombinant 20α-HSD was assayed spectrophotometrically by measuring the rate of oxidation of NADPH at 340 nm at 37° C. using a saturating concentration of benzaldehyde, 2-nitrobenzaldehyde, $_{D,L}$-glyceraldehyde methylgloxal, 9,10-phenanthrequinone or $^D$-galactose [Azhar et al., *Biochemistry* 26:7047–7057 (1987)].

As shown in Table 1 (data from 20α-hydroxyprogesterone is shown for comparison purposes only), the purified recombinant 20α-HSD proteins were quite active against the general substrates of aldose/aldehyde reductase. More particularly, 20α-HSD reduced benzaldehyde, 4-nitrobenzaldehyde, and $_{D,L}$-glyceraldehyde very efficiently. Maximal activity was noted with either benzaldehyde or $_{D,L}$-glyceraldehyde, although these results were only approximately a third of the activity observed with 20α-hydroxyprogesterone. Further, the activities of 20α-HSD produced in bacterial and insect cells were similar.

TABLE 1

Aldose/Aldehyde Reductase Activity of Recombinant 20α-HSD

| Substrate | 20α-HSD activity (nmol/min/mg protein) expressed in | |
|---|---|---|
| | E. coli | Sf-9 cells |
| 20α-Hydroxyprogesterone (100 μM) | 327 | 258 |
| Benzaldehyde (250 μM) | 122 | 81 |
| 4-Nitrobenzaldehyde (1 mM) | 103 | 89 |
| D,L-Glyceraldehyde (250 mM) | 115 | 96 |
| Methylglyoxal (1 mM) | 67 | 50 |
| 9,10-Phenanthrenquinone (100 μM) | 48 | 32 |
| D-Galactose (400 mM) | 65 | 45 |

Results are the means of duplicate determinations from three separate experiments.

D. Phosphorylation and Catalytic Function of 20α-HSD

As potential sites for phosphorylation by serine/threonine and tyrosine kinase have been previously identified [Mao et al. *Biochem. Biophys. Res. Com.* 201:1289–1295], evaluations were undertaken to test the possibility that phosphorylation modulates 20α-HSD activity.

Purified recombinant 20α-HSD (of the bacterial expression system) was incubated with various protein kinases after an initial incubation with alkaline phosphatase (to ensure that the protein was in a non-phosphorylated state) and subsequently assayed for 20α-HSD activity.

More particularly, purified bacterially expressed recombinant 20α-HSD was first incubated in 500 ml 20 nM Tris-HCl (pH 8), 1 mM $MgCl_2$, 1 mg/ml BSA, 0.5 mM dithiothreitol, and 60 U alkaline phosphatase coupled to agarose beads for 30 min. at 30° C. After centrifugation, the supernatant containing 20α-HSD was used as a substrate in various in vitro kinase assays. The protein kinase A (PKA), protein kinase C (PKC) and insulin receptor-associated tyrosine kinase activities were measured as described previously [Raz et al., *Biochem. J.* 269:603–607 (1990), Azhar et al., *Am J. Physiol*, 260:E1–E7 (1991)]. src kinase ($p60^{src}$) activity was assayed as described by Simonson and Herman [Simonson et al., *J. Biol Chem.*, 268:9347–9357 (1993)].

To test the relationship between phosphorylation and alteration of 20α-HSD activity, aliquots of 20α-HSD (1–2 μg) were incubated with 25 mM PIPES, pH 6.8, containing 10 mM Mg acetate, 100 μM ATP [$γ^{32}P$]ATP [Amersham, Arlington Heights, Ill.] to monitor phosphorylation, and EGTA (0.5 mM) plus purified rat liver PKC (4 μg; 10 U) or PKC, phosphatidylserine (250 μg/ml), diolein (10 μg/ml), plus $CaCl_2$, and 250 μM ATP (or [$γ^{32}P$]ATP) to monitor phosphorylation and the catalytic subunit of PKA (10 U) for 60 min. at 30° C. Reactions without ATP were performed under identical conditions. The catalytic activities of phosphorylated and non-phosphorylated forms of 20α-HSD were determined radiochemically as described above.

After treatment with various kinases (PKC, PKA, insulin receptor tyrosine kinase, src kinase ($p^{60src}$)), the recombinant 20α-HSD was assayed for activity. The results indicated that the recombinant 20α-HSD was readily phosphorylated by in vitro incubation with purified PKA or PKC in the presence of [$γ-^{32}P$]ATP. Phosphoamino-acid analysis of phosphorylated 20α-HSD confirmed the [$^{32}P$] phosphorylation was restricted to serine and threonine residues, and label was found predominantly on serine residues. In contrast, members of the tyrosine kinase family, including src kinase and insulin-receptor-associated tyrosine kinase, failed to phosphorylate 20α-GSD. However, all kinases tested rapidly phosphorylated their respective substrates (PKC: histone IIIs; PKA: histone V; insulin receptor tyrosine kinase: PolyGlu:Tyr (4:1); src kinase: cdc2 (6–20) peptide). Also when the recombinant 20α-HSD was phosphorylated with PKC in the presence of ATP-$Mg^{2+}$, diacylglycerol, and phosphatidylserine, 20α-HSD activity was unaffected. Further, 20α-HSD was not significantly affected by phosphorylation with PKA. Taken together, these results suggest that phosphorylation of 20α-HSD is not essential for catalytic activity.

E. Substrate Specificity of Recombinant 20α-HSD

To determine substrate specificity of recombinant 20α-HSD, the oxidation/reduction of several steroid substrates was also studied. Assays were as described above in Example 3, Part B, i.e. reduction of NADP or oxidation of NADPH [Mori et al., *J. Steroid Biochem.* 11:1443–1449 (1979); Pongsawasdi et al., *Biochim Biophys. Acta.* 799:51–58 (1984); Noda et al., *Biochim Biophys. Acta.*

1079:112–118 (1991)]. Results shown in Table 2 indicate that the recombinant 20α-HSD not only reduced progesterone and 17α-hydroxyprogesterone, but also oxidized 20α-hydroxyprogesterone. However, compared to 20α-hydroxyprogesterone, 20α-HSD activity toward 17α-hydroxyprogesterone was lower, and its activity with progesterone was relatively higher. Further, the recombinant 20α-HSD did not act on corticosterone or 5α-dihydrotestosterone.

TABLE 2

Substrate specificity of recombinant 20-α-HSD

| Substrate | Recombinant 20α HSD activity (nmol/min/mg protein) expressed in | |
|---|---|---|
| | E. coli | Sf-9 cells |
| Progesterone | 459 | 352 |
| 20α-Hydroxyprogesterone | 321 | 250 |
| 17α-Hydroxyprogesterone | 97 | 85 |
| Corticosterone | ND | ND |

The enzyme activity was measured spectrophotometrically. The data are expressed as the mean of duplicate determinations from three separate experiments. ND, not detected.

F. Catalytic Activity and Glycosylation

Since the 20α-HSD contains a putative N-glycosylation site [Mao et al., *Biochem. Biophys. Res. Comm.* 201(3) :1289–1295 (1994)] experiments were conducted to determine whether glycosylation was required for catalytic activity. A comparison of the catalytic parameters of a non-glycosylated (recombinant 20α-HSD from bacteria) and glycosylated (recombinant 20α-HSD from insects cells) forms of 20α-HSD.

Specifically, kinetic constants were determined with 20α-hydroxyprogesterone as a substrate and NADP as a cofactor. The results obtained with different amount of 20α-hydroxyprogesterone (1–100 μM) and a fixed concentration of NADP (1 mM) using bacterially expressed recombinant enzyme indicate that enzyme activity reached a saturation level around 10 μM 20α-hydroxyprogesterone. The data were transformed into a reciprocal Lineweaver-Burk plot to calculate the $K_m$ and maximum velocity ($V_{max}$) values. The initial velocity experiments were also performed under conditions where NADP concentrations varied (1–1000 μM) at a fixed saturating concentration of 20α-hydroxyprogesterone (100 μM). The maximal 20α-HSD activity was obtained with about 100 μM NADP. Similar data were obtained using the purified preparations of 20α-HSD expressed in insect cells. Kinetic parameters obtained from bacteria and insect cell-derived 20α-HSD are summarized in Table 3. The calculated $K_m$ values of bacterially expressed enzyme for 20α-hydroxyprogesterone and NADP were 5.9 and 9.5 μM, respectively, The corresponding values for baculovirus-expressed 20α-HSD were 5.8 and 9.6 μM, respectively. Thus, the enzyme preparations from two different sources had similar values. However, the recombinant 20α-HSD expressed in *E. coli* had $V_{max}$ values that were 20–30% higher than those of the recombinant 20α-HSD expressed in insect cells and when measured using similar assay conditions. These results suggest that glycosylation of 20α-HSD may not be required for the expression of catalytic activity.

TABLE 3

Steady State Kinetic Parameters of Recombinant 20α-HSD

| Parameters | Recombinant 20a-HSD expressed in | |
|---|---|---|
| | E. coli | Sf-9 cells |
| Mean Specific Activity ± SE (nmol/min - mg protein) | 332 ± 47 | 259 ± 36 |
| $K_m$, 20α-hydroxyprogesterone (μM) | 5.9 | 5.8 |
| $K_m$, NADP (μM) | 9.5 | 9.6 |
| $V_{max}$, 20α-hydroxyprogesterone (nmol/min - mg protein) | 347 | 265 |
| $V_{max}$, NADP (nmol/min - mg protein) | 334 | 259 |

EXAMPLE 4

Antibodies

In still another embodiment, the present invention provides antibodies immunoreactive with a 20α-HSD. In a preferred embodiment the antibody specifically binds to a 20α-HSD having an amino acid sequence set out in SEQ ID NO. 2. Preferably, an antibody of the invention is a monoclonal antibody. Means for preparing and characterizing antibodies are well known in the art [See, e.g., *Antibodies "A Laboratory Manual*, Harlow et al., Cold Spring Harbor Laboratory, (1988)].

Briefly, polyclonal antibodies are prepared by immunizing an animal with an immunogen comprising a polypeptide of the present invention, and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies. Antisera collected from the rabbit may be affinity purified according to methods well known to those of ordinary skill in the art (Harlow et al., supra).

As is well known in the art, a given polypeptide may vary in its immunogenicity. It is often necessary therefore to couple the immunogen (e.g., a polypeptide or polynucleotide of the present invention) with a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers.

Means for conjugating a polypeptide to a carrier protein are well known in the art and include glutaraldehyde and m-maleimidobenzoyl-N-hydroxysuccinimide ester.

As is also well known in the art, immunogenicity to a particular immunogen can be enhanced by the use of non-specific stimulators of the immune response known as adjuvants. Exemplary and preferred adjuvants include complete Freund's adjuvant, incomplete Freund's adjuvants and aluminum hydroxide adjuvant.

The amount of immunogen used of the production of polyclonal antibodies varies inter alia, upon the nature of the immunogen as well as the animal used for immunization. A variety of routes can be used to administer the immunogen (e.g., subcutaneous, intramuscular, intradermal, intravenous and intraperitoneal). The production of polyclonal antibodies is monitored by sampling blood of the immunized animal at various points following immunization and assaying for antibody levels. When a desired titer of antibodies is obtained, the immunized animal can be bled and the serum isolated and stored. Antibodies may then be isolated from the serum by methods well known in the art.

A monoclonal antibody of the present invention can be readily prepared through use of well-known techniques such as those exemplified in U.S. Pat. No. 4,196,265, herein incorporated by reference. Typically, a technique involves first immunizing a suitable animal with a selected antigen (e.g., a polypeptide or polynucleotide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. Exemplary and preferred selection agents are aminopterin, methotrexate and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides. Where azaserine is used, the media is supplemented with hypoxanthine.

This culturing provides a population of hybridomas from which specific hybridomas are selected. Typically, selection of hybridomas is performed by culturing the cells by single-clone dilution in microtiter plates, followed by testing the individual clonal supernants for reactivity with antigen-polypeptides. The selected clones can then be propagated indefinitely to provide the monoclonal antibody.

By way of specific example, to produce an antibody according to the present invention, mice are typically injected intraperitoneally with between about 1–200 μg of an antigen comprising a polypeptide of the present invention. B lymphocyte cells are stimulated to grow by injecting the antigen in association with an adjuvant such as complete Freund's adjuvant (a non-specific stimulator of the immune response containing killed Mycobacterium tuberculosis). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitating against radiolabeled antigen. Preferably, the process of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5\times10^7$ to $2\times10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus denominate immortal. Numerous cultured cells lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in a selection medium such as HAT media (hypoxanthine, aminopterin, thymidine). Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection media.

Each of the surviving hybridoma cells produces a single (monoclonal) antibody. These cells are then screened for the production of the specific antibody immunoreactive with an antigen/polypeptide of the present invention by well known methods. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

In yet another embodiment, antibodies may also be produced, by the methods described supra, against 20α-hydroxyprogesterone (the metabolite of progesterone reduction by 20α-HSD) and progesterone (the natural substrate of 20α-HSD).

EXAMPLE 5

Methods for Screening for Individuals Predisposed to Spontaneous Abortions

The present invention also relates to diagnostic applications, wherein individuals are screened for the predisposition to spontaneous abortions.

As discussed previously, it is possible that a significant number of spontaneous abortions are due to early expression of 20α-HSD. Therefore, in one embodiment, circulating levels of 20α-HSD are determined (e.g., for those individuals at-risk for spontaneous abortions). Specifically, antibodies (of Example 4) may be used to quantify circulating levels of 20α-HSD. A certain percentage of the population of women predisposed to spontaneous abortions may be expected to have higher levels of 20α-HSD, as compared to normal subjects. 20α-HSD levels may be determined by such well known techniques [e.g. Enzyme-Linked Immunosorbent Assay (ELISA)) as set forth in *Current Protocols in Molecular Biology*, Eds. Ausubel et al., Wiley Interscience, (1997)].

In a second embodiment, circulating levels of 20α-hydroxyprogesterone (the metabolite of progesterone reduction by 20α-HSD) are determined (e.g., for those individuals at-risk for spontaneous abortions). Determination of the circulating levels of 20α-hydroxyprogesterone, is an indirect determination of the levels of 20α-HSD, i.e., one would expect higher levels of 20αhydroxyprogesterone in individuals with increased expression of 20α-HSD, as compared to normal subjects.

Specifically, antibodies (of Example 4) may be used to quantify circulating levels of 20α-hydroxprogesterone. 20α-hydroxyprogesterone levels may be determined by such well known techniques [e.g. Enzyme-Linked Immunosorbent Assay (ELISA)) as set forth in *Current Protocols in Molecular Biology*, Eds. Ausubel et al., Wiley Interscience, (1997)].

In a third embodiment, circulating levels of progesterone (the natural substrate of 20α-HSD) are determined (e.g., for those individuals at-risk for spontaneous abortions). Determination of the circulating levels of progesterone, would be an indirect determination of the levels of 20α-HSD, i.e., one would expect low levels in individuals with increased expression of 20α-HSD, as compared to normal subjects Specifically, antibodies (of Example 4) may be used to quantify circulating levels of progesterone. Progesterone levels may be quantified by such well known techniques [e.g. Enzyme-Linked Immunosorbent Assay (ELISA)) as set forth in *Current Protocols in Molecular Biology*, Eds. Ausubel et al., Wiley Interscience, (1997)].

Briefly, in one version of an ELISA assay (i.e., antibody-sandwich ELISA), unlabeled capture antibody to the antigen of interest, i.e., 20α-HSD, 20α-hydroxprogesterone, or progesterone is bound to the bottom of a microplate well; unbound capture antibody is removed by washing the microplate. A solution (e.g. serum or plasma) containing an unknown amount of antigen (i.e., 20α-HSD, 20α-hydroxprogesterone, or progesterone) is added for a set incubation time-period. After binding of the antigen to the antibody, unbound antigen is washed out and a second enzyme-labeled antibody directed against the antigen is added. Unbound enzyme-labeled antibody is removed by washing and a substrate to the enzyme is added. Once the enzyme has acted upon the substrate, a color will develop. Standard colorimetric techniques and analysis are employed to determine levels of the antigen (i.e., microtiter plate reader). Those of skill in the art will readily recognize that other forms of the ELISA may be used to quantify levels of circulating 20α-HSD, 20α-hydroxprogesterone, or progesterone (e.g., direct competitive ELISA).

Further, in order to determine the normal and abnormal range of levels (of 20α-HSD 20α-hydroxprogesterone, or progesterone, levels will be determined (by the method described herein) in normal (not at-risk for spontaneous abortions) individuals. Levels will be determined in both pregnant and non-pregnant individuals, at various ages, and at various stages of the menstrual cycle.

Also contemplated with the above embodiments of methods of screening for individuals predisposed to spontaneous abortions are diagnostic kits for the determination of serum levels of 20α-HSD, 20α-hydroxyprogesterone, or progesterone. The diagnostic kits may comprise a known amount of antibody substance immunologically reactive to the substance or enzyme of interest, buffers, diluents, label for the detection of the substance of interest, and directions for the use of said diagnostic kit.

EXAMPLE 6

Anti-Reproductive Effect of Recombinant 20α-HSD During Pregnancy

The aim of these experiments was to determine whether administration of recombinant 20α-HSD to pregnant animals would lead to interruption in pregnancy. Although the following is exemplified by administration of rats, those of skill in the art will readily appreciate that other mammals may be treated in the same manner.

Pregnant Sprague-Dawley rats were treated with purified 20α-HSD produced by a bacterial expression system (see Example 1) to assess the effect of the enzyme on (1) progesterone levels and (2) the possible termination of pregnancy. More particularly, animals were divided into two treatment groups (7 rats per group: 6 receiving treatment, 1 control) and were injected (intraperitoneally) with the purified recombinant 20α-HSD and an eqimolar dose of NADPH. Injections were administered on day 8 of pregnancy and continued for 72 hours.

Group 1 received intraperitoneal injections of the purified 20α-HSD (167 μg with an equimolar dose of NADPH) every 4 hours, continuing for 72 hours. Group 2 received intraperitoneal injections of the purified 20α-HSD (250 μg with an equimolar dose of NADPH) every 6 hours, continuing for 72 hours. The control treatment groups received an equal amount of GST alone with an eqimolar dose of NADPH. Blood samples were collected every 12 hours via jugular veins. Serum progesterone levels were determined by standard radioimmunoassay techniques [Gibori et al., *Endocrinology* 100:1483–1495 (1977)].

Administration of 20α-HSD caused a marked decrease in circulating progesterone and termination of pregnancy within 72 hours of treatment. Specifically, administration of 20α-HSD caused serum progesterone levels to decline significantly within 48 hours after beginning treatment in Group 1 (4 hour treatments). Further, serum progesterone levels significantly declined after 60 hours in Group 2 (6 hour treatments). Administration under the Group 1 protocol (4 hour injections) caused spontaneous abortions. More specifically, vaginal bleeding was noted prior to the 72 hour end point and laparoscopy (at the 72 hour end point to check for fetal) confirmed the abortive effects. 5 animals aborted totally, with 2 animals partially aborting. Animals treated with GST and NADPH did not show a similar decrease in circulating progesterone levels or termination of pregnancy.

As discussed above, although rats were used to exemplify use of 20α-HSD as, those of skill in the art will readily appreciate that other mammals, including humans, may be treated in a similar manner. Specifically, a pharmaceutical composition comprising the 20α-HSD and a pharmaceutically acceptable carrier, diluent and/or adjuvant may be administered to a mammal (including a human) to reduce circulating levels of progesterone and thereby inhibit the maintenance of pregnancy and/or preventing implantation leading to pregnancy.

Although the present invention has been described in terms of preferred embodiments, it is intended that the present invention encompass all modifications and variations that occur to those skilled in the art upon consideration of the disclosure herein, and in particular those embodiments that are within the broadest proper interpretation of the claims and their requirements. All literature cited herein is incorporated by reference.

What is claimed is:

1. A method of inducing abortion or preventing nidation in a mammal comprising reducing circulating blood levels of progesterone in said mammal by administration to the mammal an effective amount of a composition comprising 20α-hydroxysteroid dehydrogenase wherein said composition further comprises a reduced form of nicotinamide adenine dinucleotide phosphate (NADPH).

2. The method of claim 1 wherein said administration is by a route of administration selected from the group consisting of oral, intramuscular, intraperitoneal, intravenous, and subcutaneous routes.

3. The method of claim 1 wherein said composition is administered through an osmotic mini-pump or time-released pellet.

4. The method of claim 1 wherein said mammal is a human.

* * * * *